United States Patent
Hered

(10) Patent No.: US 6,440,065 B1
(45) Date of Patent: Aug. 27, 2002

(54) SINGLE-USE DISPOSABLE EYELID SPECULUM, EYE EXAMINATION KIT, AND METHOD FOR EXAMINING A PATIENT'S EYE

(75) Inventor: Robert W. Hered, Altlantic Beach, FL (US)

(73) Assignee: The Nemours Foundation, Jacksonville, FL (US)

( * ) Notice: Subject to any disclaimer, the term of this patent is extended or adjusted under 35 U.S.C. 154(b) by 0 days.

(21) Appl. No.: 09/968,158

(22) Filed: Oct. 1, 2001

(51) Int. Cl.[7] ................................................. A61B 1/32
(52) U.S. Cl. ..................................................... 600/236
(58) Field of Search .................................. 600/201, 206, 600/209, 210, 214, 219, 226, 235, 236, 237; 206/363, 370

(56) References Cited

U.S. PATENT DOCUMENTS

| | | | |
|---|---|---|---|
| 1,389,436 A | * | 8/1921 | Cameron |
| 2,117,312 A | | 5/1938 | Gauly |
| 2,555,076 A | | 5/1951 | Crossley |
| 3,443,421 A | | 5/1969 | Posner et al. |
| 3,511,085 A | | 5/1970 | Posner et al. |
| 3,651,689 A | | 3/1972 | Haddad |
| 4,037,589 A | * | 7/1977 | McReynolds |
| 4,046,254 A | * | 9/1977 | Kramer |
| 4,321,916 A | | 3/1982 | McKee |
| 4,453,546 A | | 6/1984 | Katz et al. |
| 4,520,815 A | * | 6/1985 | Marinoff |
| 4,997,092 A | * | 3/1991 | Dupont ........................ 206/632 |
| 5,070,860 A | | 12/1991 | Grounauer |
| 5,163,419 A | | 11/1992 | Goldman |
| 5,341,798 A | | 8/1994 | Grounauer |
| 5,433,190 A | | 7/1995 | Sunalp |
| 5,441,040 A | | 8/1995 | Williams, Jr. |
| 5,618,261 A | | 4/1997 | Nevyas |

OTHER PUBLICATIONS

"Ophthalmic–Eye Specula", Item 103, John Reynders & Co. Catalog, 1895, New York, p. 166.*

Woodman et al., "Disinfection of Eyelid Speculums for Retinopathy of Prematurity Examination", *Arch. Opthalmol.*, vol. 116, 1998, pp. 1195–1198.

Hutchinson et al., "Disinfection of Eyelid Specula with Chlorhexidine Gluconate (Hibiclens) After Examinations for Retinopathy of Prematurity", *Arch. Ophthalmol.*, vol. 118, 2000, pp. 786–789.

Van Ogtrop et al., "Serratia Marcenscens Infections in Neonatal Departments: Description of an Outbreak and Review of the Literature", *J. Hosp. Infec.*, 1997, Abstract Only, 1 page.

Wasserman et al., "Pseudomonas–induced Bilateral Endophthalmitis with Corneal Perforation in a Neonate", *J. Aapos.*, 1999, Abstract Only, 1 page.

Iroha et al., "Bacterial Eye Infection in Neonates, a Prospective Study in a Neonatal Unit", *West Afr. J. Med.*, 1998, Abstract Only, 1 page.

Birenbaum et al., "Adenovirus Type 8 Conjunctivitis Outbreak in a Neonatal Intensive Care Unit", *Arch. Dis. Child*, 1993, Abstract Only, 1 page.

(List continued on next page.)

Primary Examiner—Jeffrey A. Smith
(74) Attorney, Agent, or Firm—Hunton & Williams

(57) ABSTRACT

The present invention relates to a single-use disposable eyelid speculum and scleral depressor. The eyelid speculum comprises an elongated curved arm formed from an elastic single piece element. The elongated curved arm terminates in integrally formed spoons, each spoon being configured to engage an eyelid. The eyelid speculum and scleral depressor may be provided as a kit in either separate or combined packing in a sterilized condition. The kit is intended to be disposable after a single use.

18 Claims, 3 Drawing Sheets-

OTHER PUBLICATIONS

Ford–Jones et al., "Epidemiologic Study of 4684 Hospital–Acquired Infections in Pediatric Patients", *Pediatr. Infect. Dis. Journal*, 1989, Abstract Only, 1 page.

Rudd et al., "A Prospective Study of Chlamydial, Mycoplasmal, and Viral Infectious in a Neonatal Intensive Care Unit", *Arch. Dis. Child.*, 1984, Abstract Only, 1 page.

Shah et al., "Bacteremia, Meningitis, and Brain Abscesses in a Hospitalized Infant: Complications of Pseudomonas Aeruginosa Conjunctivitis", *J. Perinatol*, 1999, Abstract Only, 1 page.

Sher et al., "The Effect of Various Method of Eye Immobilization on Conreal Topography", *Journal of Refractive Surgery*, vol. 12(4), 1996, pp. 1–7.

Dhillon et al., "Screening for Retinopathy of Prematurity: Are a Lid Speculum and Seleral Indentation Necessary?", *J. Pediatr Opthalmol Strabismus*, 1993, 30, pp. 377–381.

Akorn, "Surgical Instruments", pp. 106–108.

"Reusing Disposables Balancing Safety & Costs", *Ophthalmology Management*, 2001, 26–33.

Akron, "Surgical Instruments", pp. 106–108.

Storz Ophthalmics, "Specula", pp. 238–248.

Storz Opthalmics, "Radial, Scleral Depressors/Markers", pp. 41–43.

Karaki, "A New Sceral Depressor for Extremely Premature Infants", *J. Pediat Ophthalmol Strabismus*, 1994, 31, p. 267.

* cited by examiner

SINGLE-USE DISPOSABLE EYELID SPECULUM, EYE EXAMINATION KIT, AND METHOD FOR EXAMINING A PATIENT'S EYE

FIELD OF THE INVENTION

The present invention relates generally to eye examination devices and more specifically to eyelid speculum used to hold a patient's eyelids open, and to a disposable kit including a speculum for eye examination.

BACKGROUND OF THE INVENTION

Various devices have been used in the past for the purpose of holding a patient's eyelid open to allow access to an eyeball for examination, treatment and ocular surgery. Such procedures are performed on human and animal patients of all ages and all sizes regularly. However, tools for such examinations are typically designed for use in adult human eyes.

Examination of infant eyes is very important in a number of situations. For example, examination for retinopathy prematurity (ROP) is an important clinical task for pediatric ophthalmologists, certain general ophthalmologists and retina specialists. Timely ROP examinations are essential in reducing the incidence of blindness in premature infants. ROP examinations are typically initially performed at the crib or incubator in the neonatal intensive care unit (NICU) with additional exams performed in an out-patient clinic or office. The ROP examination involves the use of an indirect ophthalmoscope, an eyelid speculum and a scleral depressor. It has been estimated that 300,000 ROP examinations are performed in NICU's in the United States every year.

Examination tools known in the art suffer from at least two deficiencies when used for infants. First, they are typically steel instruments which are heavy and not well-sized to an infant's eye. Not only are these devices cumbersome to use, but also the appearance may be frightening to family or staff attending the infant. Secondly, the devices currently used are relatively expensive; hence, they are intended for multiple uses. Autoclave sterilization is the only adequate method of cleaning the instruments between use. Instrument cleaning methods other than sterilization, such as alcohol swabs and chlorhexidine gluconate, have been shown to be inadequate for eradicating all microorganisms. Without resterilization, a risk of nosocomial eye infection exists. Substantial cost is incurred in having a sufficient number of instruments available and in reprocessing instruments for reuse.

Further, lack of availability of instruments at hospitals is not uncommon and, hence, it is not unusual for ophthalmologists to transport non-sterile instruments from their offices and use them for multiple examinations without benefit of sterilization.

Thus, there is a need for a lightweight speculum and scleral depressor for use in examining infant eyes which are practically and economically single-use devices.

SUMMARY OF THE INVENTION

The present invention includes a single-use disposable eyelid speculum and a scleral depressor. The eye speculum and scleral depressor are intended to be presented to the user in sterile packaging and to be disposed of after a single use. This reduces the risk of nosocomial eye infection. Additionally, the eyelid speculum and scleral depressor are constructed of lightweight material which improves performance. The combination of materials used and design results in a speculum that applies a constant, predictable, uniform force to the eyelids, is conveniently sized to accommodate various ages and sizes of patients and has a less onerous appearance.

The eyelid speculum of the invention has an elongated curved arm formed from an elastic, single piece element. The elongated curved arm is curved such that the two ends of the arm are in a generally parallel and opposing position. Integrally formed spoons are formed as a portion of the ends of the elongated curved arm. Each of the spoons has a curvature adapted to the shape of the eyelid.

The eyelid scleral depressor of the invention has an elongated handle portion with at least one end of the handle terminating in stem portion. The stem portion terminates in a tip which is configured for touching an eyeball.

The speculum and scleral depressor may be provided as a kit in either separate or combined packaging in a sterilized condition. The kit is intended to be disposable after a single-use.

A method for examining a patient's eye using the eyelid speculum and scleral depressor is provided. The method for examining a patient's eye comprises of the steps of positioning the eyelid speculum proximate to the patient's eye, engaging each of the upper and lower eyelids of the patient's eye with each of the spoons of the eyelid speculum, applying the scleral depressor to the surface of the eyeball portion of the patient's eye and manipulating the eyeball by applying pressure to the sclera of the eyeball.

DETAILED DESCRIPTION OF THE INVENTION

The present invention includes a single-use eyelid speculum and scleral depressor which may be sized for convenient use in eye examinations or medical procedures for human and/or animal patients of any age including infant patients. The eyelid speculum and scleral depressor of the invention may be packaged in sterile packaging to provide a single-use, sterile eye examination kit.

In an exemplary embodiment of the invention, the invention has three components: an eyelid speculum, a scleral depressor, and a packaging portion which can maintain the eyelid speculum and scleral depressor in a sterilized condition until time of use.

Figure 1:
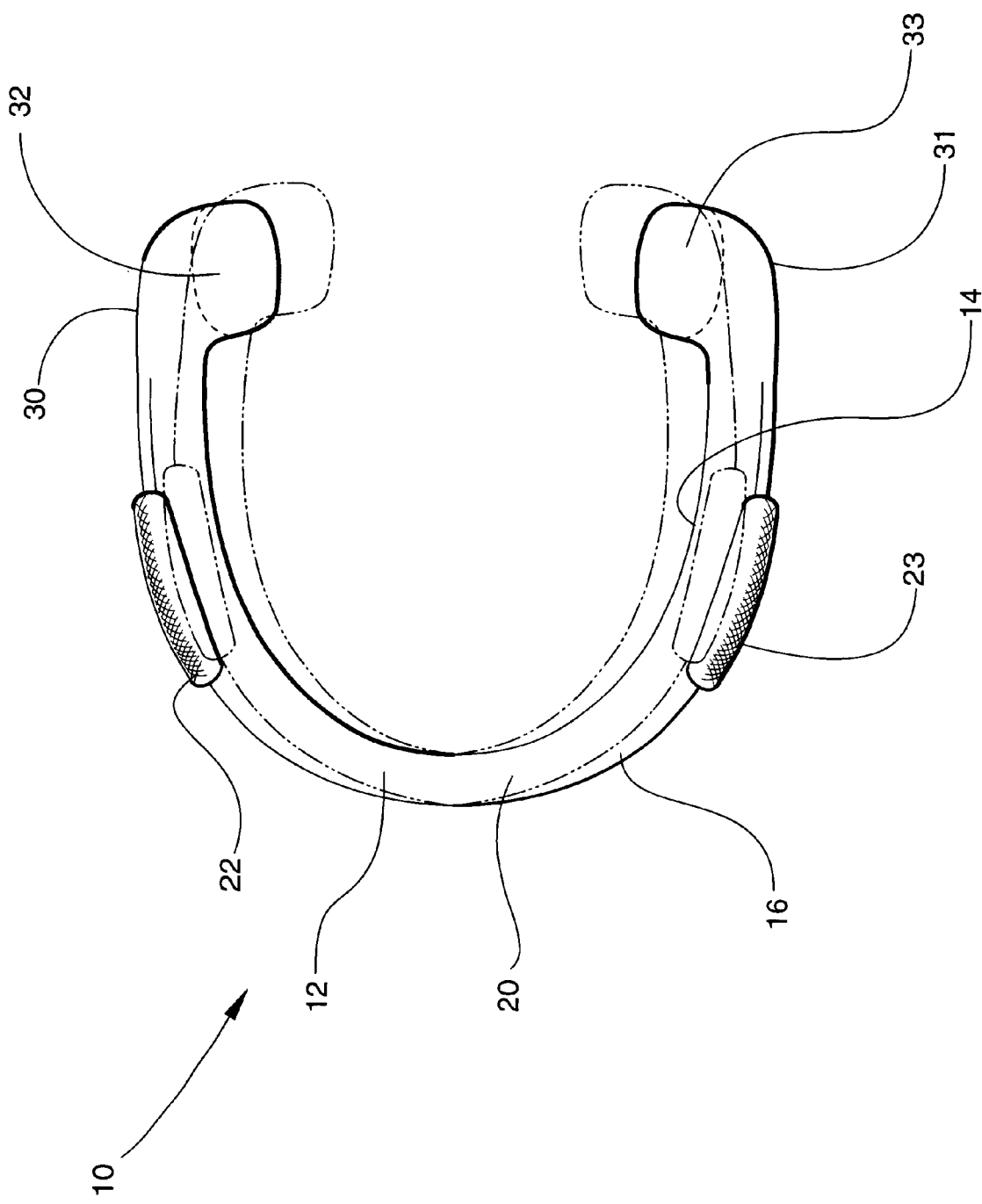
FIG. 1 shows an embodiment of an eyelid speculum.
Figure 2:
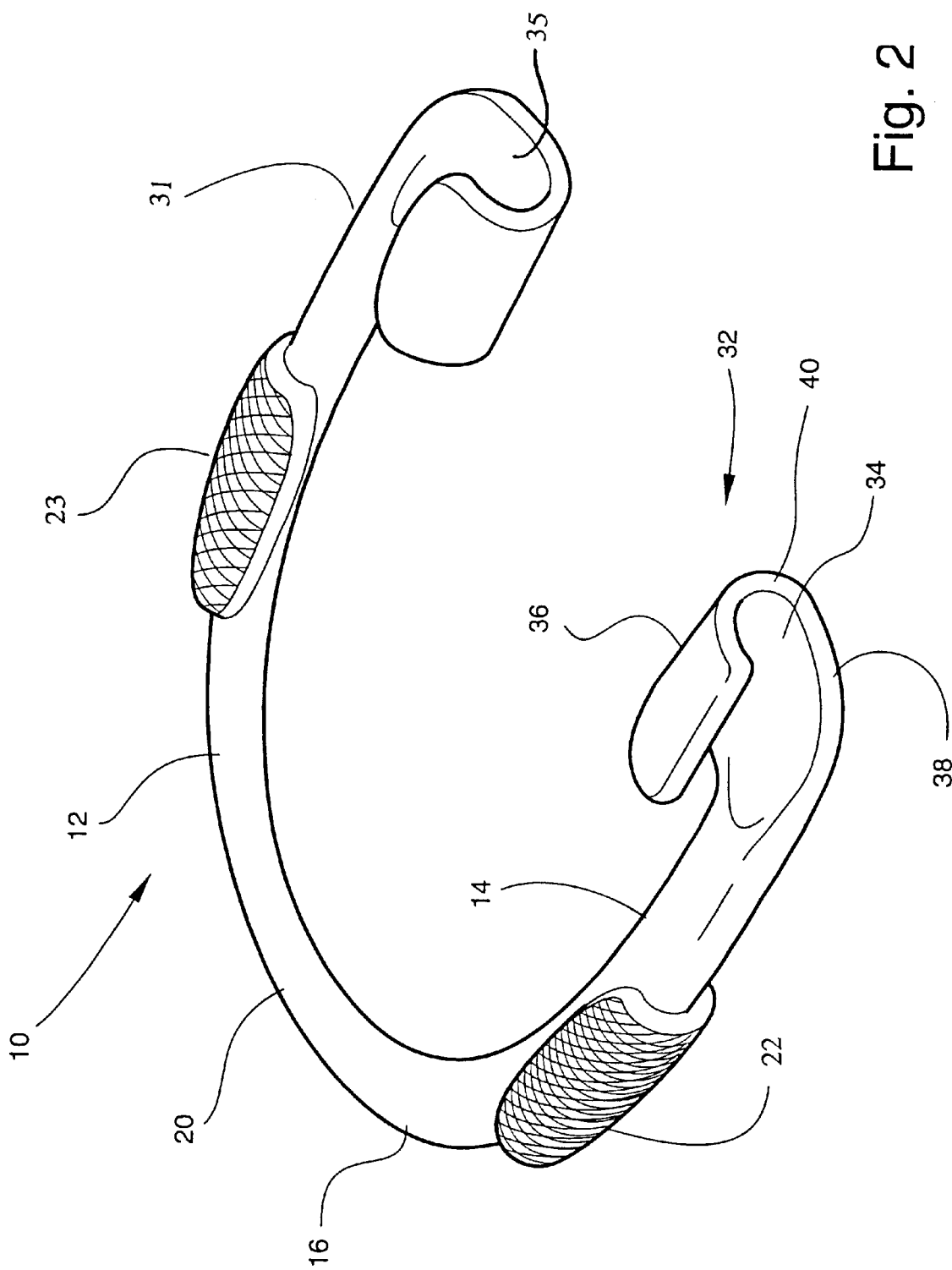
FIG. 2 shows a perspective view of an eyelid speculum.

FIGS. 1–2 show an exemplary embodiment of an eyelid speculum device 10 of the present invention used to hold a patient's upper or lower eyelids open to allow access to an eyeball for examination, treatment, ocular surgery or the like. The eyelid speculum device 10 has an elongated curved arm 12, having two arm ends 30, 31. A curvature 20 of the elongated curved arm 12 at a position between the arm ends 30, 31 permits the arm end 30 to be aligned in opposing position with respect to arm end 31 as shown in FIG. 1. The elongated curved arm 12 has grasping portions 22, 23. In some embodiments, the grasping portions 22, 23 simply designate a position oppositely positioned on either side of the elongated curved arm 12 between each of the ends 31, 32 and the curvature 20, as shown in FIG. 1. As one skilled in the art will appreciate, the grasping portions 22, 23 may be designed to facilitate grasping. For example, the grasping portions 22, 23 may have integrally formed texturing, indentations enlarged portion, or a molded curvature and the like. These are representative examples of designs that facilitate grasping which are provided for illustrative purposes. As one skilled in the art will recognize, a number of alternatives for facilitating grasping compatible with the design or function of the speculum may be employed. Additionally, the elongated curved arm 12 has an outer surface 16 and an inner surface 14. Optionally, the elongated curved arm may be contoured to fit the contour of a patient's face. For example, referring to FIG. 1 in some exemplary embodiments the region of the curvature 20 will curse upward or downward with respect to the plane parallel to the surface shown in FIG. 1 of the Speculum 10. As FIG. 1 shows, the speculum is flexible, and applying pressure, preferably at the grasping portions 22, 23 permits adjustment of the distance between the two arm ends 30,31.

Each of the arm ends 30, 31 each terminate in an integrally formed spoons 32, 33. Spoon 32 is shown in a perspective view in FIG. 2. Each of spoons 32, 33 has a spoon-cupped surface 34, 35 an spoon outer surface 36, a spoon edge 38 and a spoon curvature 40. The integrally formed spoons 32, 33 are oriented such that the spoon-cupped surface 34, 35 are directed outward, i.e., in the direction of the elongated arm 12 outer surface 16. Thus, when the eyelid speculum 10 is positioned over an eyeball, the spoon-cupped surfaces 34, 35 are oriented toward the eyelids and away from the cornea. Optionally, the outer surface 36 of the spoons 32, 33 may be contoured to fit against the patient's eyeball.

To use the eyelid speculum 10 to perform an examination, the examiner positions his fingers on the grasping portions 22, 23 of the eyelid speculum 10 and gently applies pressure to the eyelid speculum 10 at the grasping portion 22, 23. This squeezes the ends 30, 31 of the eyelid speculum 10 closer together. The eyelid speculum 10 is then positioned nearer the patient's eyeball with the spoons 32, 33 generally aligned with the upper and lower eyelids and the pressure applied to the eyelid speculum 10 is gently decreased. This allows the elongated arm 30 to return to its original position and the spoon-cupped surfaces 34, 35 of the spoons 32, 33 to engage the upper and lower eyelids, respectively. To remove the eyelid speculum 10, pressure is again applied to the grasping portions 22, 23 and the ends 31, 31 move closer together, disengaging the spoons cupped surfaces 34, 35 from the upper and lower eyelids.

A suitable material for constructing an eyelid speculum 10 should be resilient, have a modulus of elasticity that allows for bending of the arm 12 without permanent deformation and causes the elongated curved arm 12 to return to its original position after the grasping portions 22, 23 are released. Further, it is desirable that the material be lightweight, sterilizable without deterioration, and non-reflective. It is further desirable that the material be disposable after a single use. In an exemplary embodiment, the eyelid speculum 10 is constructed from a polymeric material. In certain embodiments it is desirable to use a moldable polymeric material for ease of manufacturing and production of the device at a cost economically reasonable for a singe-use device. The combination of material selection and curvature 20 of the curved elongated arm 12 is such that, when the device is positioned in the patient's eye, the spoon-cupped surfaces 34, 35 exert a force to hold the upper and lower eyelids open. In an exemplary embodiment suitable for use with prematurely born infants it is desirable that the spoon-cupped surfaces 34, 35 exert a force, of about 90–150 grams against the eyelids when properly positioned. The force exerted may be adjusted in other embodiments to accommodate the requirements of a specific category of patient.

The eyelid speculum device 10 should be dimensioned such that, when in use, the spoon-cupped surfaces 34, 35 retract the upper or lower eyelids to expose the entirety of the cornea and preferably about a millimeter of sclera on either side of the cornea. Preferably, in this position of use the internal aspects of the two spoons are parallel to each other, thereby creating a symmetrical spreading of the eyelids with an even distribution of force to the eyelids. Sizing of the spoon 32, 33 is important as, for example, a spoon which is too wide for the patient may not open the eyelids wide enough without causing tissue damage. As one skilled in the art will appreciate, dimensioning can be conveniently varied to accommodate various sizes and ages of human an/or animal patients. For example, in one embodiment intended for use with young human infants, the spoons may be spaced from each other by about 12 millimeters when in the in-use position, the spoon-cupped surfaces have a depth of about 5 millimeters from spoon edge 38 to spoon curvature 40, and a length of each spoon along the inner edge of about 6 millimeters. Suitable dimensions for other embodiments may be determined by one skilled in the art from known and well-documented information regarding the size and anatomical characteristics for human and animal ocular regions.

Figure 3:
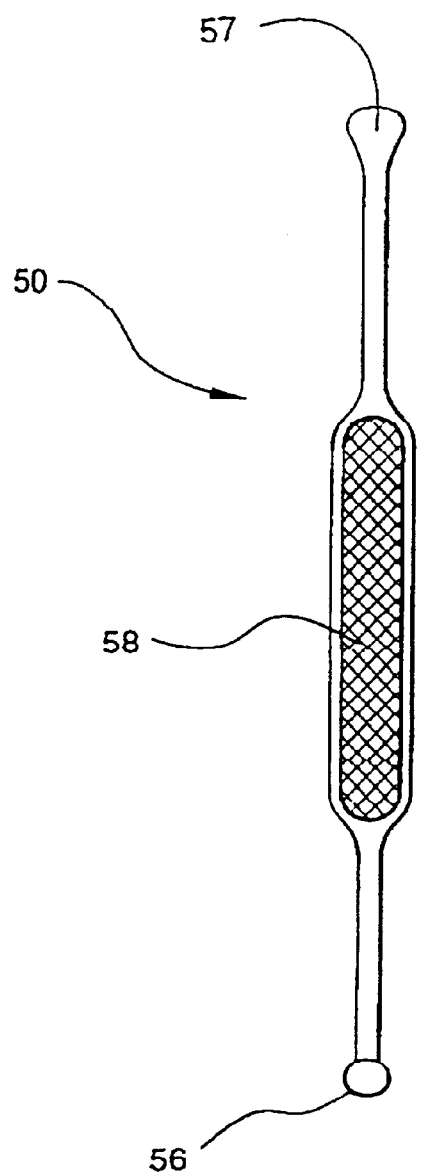
FIG. 3 shows one embodiment of a scleral depressor.
Figure 4:
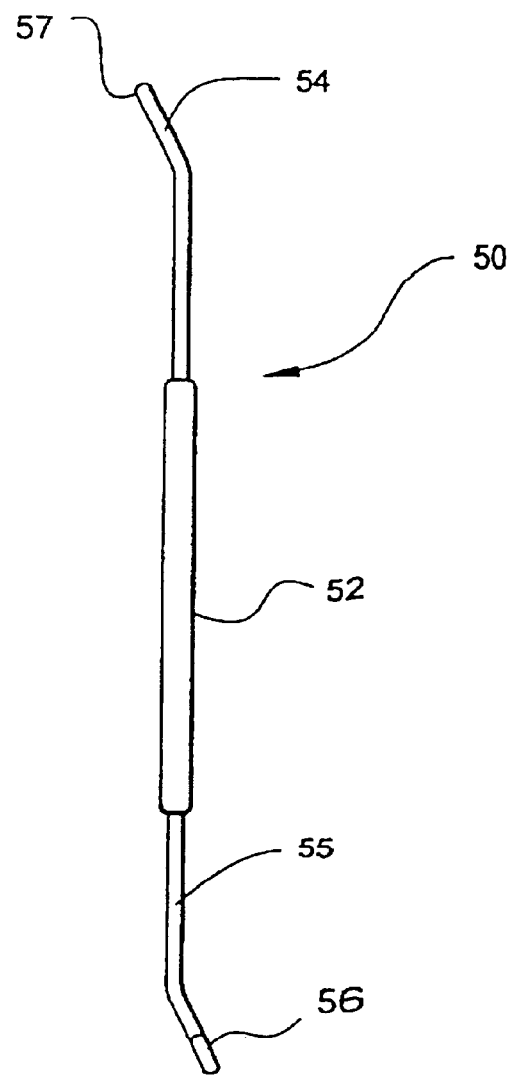
FIG. 4 shows the scleral depressor of FIG. 4 as it appears rotated 90° from the portion shown in FIG. 3.

The invention may also include in an exemplary embodiment a scleral depressor. An embodiment of the scleral depressor 50 is shown in FIGS. 3–4. As shown in FIGS. 3–4, the scleral depressor 50 has an elongated handle portion 52, two bent stem portions 54, 55 and two tips 56, 57. The tips 56, 57 may optionally be enlarged with respect to the portions 54, 55 stems and also optionally may be curved or shaped to facilitate their use in touching an eyeball. In other embodiments the scleral depressor may have only a single bent stem portion and a single tip or optionally have a straight stem portion.

A grasping portion 58 is located on the handle portion 52 of the scleral depressor 50 at a point between the bent stem portions 54, 55. The grasping portion 58 may be simply a position on the elongated handle portion 52. Optionally, the grasping portion 58 may be configured to facilitate grasping. As one skilled in the art will recognize, there are many configurations and/or methods to facilitate grasping and any compatible method known to one skilled in the art may be employed. Representative examples of configurations for facilitating grasping include integral texturing or configurations having flattened, enlarged, indented or contoured shapes at the grasping position.

Degree of tilt of the bent stem portions 54, 55 and the shape of the tips 56, 57 may be varied to accommodate conveniently putting the scleral depressor 50 in a position of use touching an eyeball. Additionally, the scleral depressor 50 may be sized with different dimensions to facilitate use of the scleral depressor 50 with different sizes and ages of human and animal patients. A typical scleral depressor used for an infant, for example, may have a total length of about 100 to 150 millimeters with tips 56, 57 about 4 to 6 mm across. For convenience in examination it may be desirable in some embodiments that the tips 56, 57 be of different sizes and/or contours.

It is desirable that the scleral depressor be made of a rigid material that is lightweight, sterilizable without deterioration, and non-reflective. Further, it is desirable that the scleral depressor be formed from material that is practically and economically disposable after a single use. Rigid polymeric materials are one example of a suitable material.

Although the eyelid speculum 10 and the scleral depressor 50 may be used independently, typically, the scleral depressor 50 will be used in conjunction with eyelid speculum 10. When using the speculum and scleral depressor for examining a patient's eye, the eyelid speculum is first positioned proximate to the patient's eyeball and is positioned to engage the patient's upper and lower eyelids as described above. When the eyelid speculum 10 is in place, the scleral depressor is then touched to the surface of the eyeball and the eyeball is manipulated by applying pressure to the scleral depressor. The eyelid speculum 10 may be used alone or in conjunction with the scleral depressor for eye examinations, eye treatments, eye surgery and the like.

In an exemplary embodiment of the invention, the eyelid speculum 10 and scleral depressor 50 are provided as a kit wherein the eyelid speculum 10 and scleral depressor 50 are in a sterilized condition and packaged to maintain the sterile condition until immediately prior to use. Methods of sterilizing equipment for medical uses, either prior to or subsequent to packaging, and maintaining the equipment in a packaged sterilized state until ultimate end use are well-known in the art. Any of the known methods compatible with the physical features and characteristics of the eyelid speculum 10 and scleral depressor 50 may be used. In some exemplary embodiments, the eyelid speculum 10 and scleral depressor 50 are packaged together in a single package. In other embodiments the scleral depressor 50 and eyelid speculum 10 are packaged in a single package with separate compartments for each of the scleral depressor 50 eyelid and eyelid speculum 10. Independent packaging of the eyelid speculum 10 and scleral depressor 50 may be equally convenient and is used in other embodiments in the invention.

Those persons skilled in the art will appreciate that the present invention is susceptible to a broad utility and application. Many embodiments and adaptations of the present invention other than those herein described, as well as many variations, modifications will be apparent from or reasonably suggested by the present invention and the foregoing description thereof, without departing from the substance or scope of the present invention. Accordingly, while the present invention has been described herein in detail in exemplary embodiments, it is to be understood that this disclosure is only illustrative and exemplary of the present invention and is made merely for purposes of providing a full and enabling disclosure of the invention. The foregoing is not intended or to be construed to limit the present invention or otherwise to exclude any such other embodiments, adaptations, variations, modifications, the present invention being limited only by the claims appended hereto and the equivalents thereof.

What is claimed is:

1. An eyelid speculum device for retracting a patient's eyelids comprising:
   an elongated curved arm formed from an elastic, single-piece element, having a first and a second end, wherein the first end and the second end are in a generally parallel and opposing position; and
   a pair of spoons integrally formed as a portion of the first end and the second end, each of the pair of spoons having a curvature portion adapted to the shape of an eyelid, the spoons being spaced apart by a predetermined distance, wherein the elongated curved arm is constructed of a material and configured so as to be selectively deformed so that the spoons are displaced inwardly to reduce the distance between the spoons and allow engagement of the spoons with a patient's upper and lower eyelids, the spoons so-engaged exerting a separating force in a range of about 90 grams to about 150 grams against the upper and lower eyelids.

2. The eyelid speculum of claim 1, wherein the eyelid speculum is made of a polymeric material.

3. The eyelid speculum of claim 2, wherein the eyelid speculum is made by injection molding.

4. The eyelid speculum of claim 1, wherein the eyelid speculum is sized for a selected specie and size of patient.

5. The eyelid speculum of claim 4, wherein the eyelid speculum is sized for a human infant.

6. The eyelid speculum device of claim 1, further including two grasping portions on the elongated curved arm wherein the grasping portions include at least one physical feature to facilitate grasping.

7. A disposable eye equipment kit, the kit comprising:
   the eyelid speculum of claim 1 and wherein the speculum is contained in sterile packaging.

8. A disposable eye equipment kit, the kit comprising:
   an eyelid speculum having
   an elongated curved arm formed from an elastic, single-piece element having a first and a second end in a generally parallel and opposing position and a pair of spoons integrally formed as a portion of the first end and the second end, each of the pair of spoons having a curvature portion adapted to the shape of an eyelid, the spoons being spaced apart by a predetermined distance, wherein the elongated curved arm is configured to be selectively deformed so that the spoons are displaced inwardly to reduce the distance between the spoons and allow engagement of the spoons with a patient's upper and lower eyelids, the spoons so engaged exerting a separating force in a range of about 90 grams to about 150 grams against the upper and lower eyelids; and
   a scleral depressor wherein the scleral depressor has a tip portion sized to fit between the spoons as the spoons engage the upper and lower eyelids.

9. The disposable eye equipment kit of claim 8, wherein the scleral depressor has a grasping portion including at least one physical feature to facilitate grasping.

10. The disposable eye equipment kit of claim 8 wherein the eyelid speculum and the scleral depressor are sized for a selected specie and size of patient.

11. The disposable eye equipment kit of claim 10 wherein the eyelid speculum and scleral depressor are made of polymeric materials.

12. A method for examining a patient's eye comprising the steps of:
   providing the kit of claim 8;
   positioning proximate to the patient's eye the eyelid speculum of the kit of claim 8;
   engaging each of the upper and lower eyelids of the patient's eye with the spoons of the speculum of claim 8, thereby maintaining each of the upper and lower eyelids in an open position;
   applying the scleral depressor of the kit of claim 8 to a scleral surface of the patient's eye; and
   manipulating the patient's eye by applying pressure to the scleral surface of the patient's eye.

13. A method for examining a patient's eye comprising the steps of:

providing an eyelid speculum having an elongated curved arm formed from an elastic, single-piece element, the elongated curved arm having a first end and a second end in a generally parallel and opposing position, and a pair of spoons integrally and firedly formed as a portion of the first end and the second end, each of the pair of spoons having a curvature portion adapted to the shape of an eyelid, the spoons being spaced apart by a predetermined distance, wherein the elongated curved arm is configured to be selectively deformed so that the spoons are displaced inwardly to allow engagement of the spoons with a patient's upper and lower eyelids, the spoons so-engaged exerting a separating force in the range of about 90 grams to about 150 grams against the upper and lower eyelids;

applying a compressive force to the elongated curved arm to move the pair of spoons inwardly to reduce the distance between the spoons;

positioning the speculum proximate the patient's eye; and releasing the compressive force on the elongated curved arm to allow the curvature portion of one of the pair of spoons to engage the patient's upper eyelid and to allow the curvature portion of the other of the pair of spoons to engage with the patient's lower eyelid.

14. The method of claim 13 further comprising the steps of:

providing a scleral depressor;

applying the scleral depressor to the a scleral surface of the patient's eye; and manipulating the patient's eye by applying a compressive force to the scleral surface of the patient's eye.

15. The method of claim 14 wherein the scleral depressor has a tip portion sized to fit between the spoons as the spoons engage the upper and lower eyelids.

16. A method for examining a patient's eye comprising the steps of:

providing an eyelid speculum having an elongated curved arm formed from an elastic, single-piece element, the elongated curved arm having a first end and a second end in a generally parallel and opposing position, and a pair of spoons integrally and firedly formed as a portion of the first end and the second end, each of the pair of spoons having a curvature portion adapted to the shape of an eyelid, the spoons being spaced apart by a predetermined distance, wherein the elongated curved arm is configured to be selectively deformed so that the spoons are displaced inwardly to allow engagement of the spoons with a patient's upper and lower eyelids;

applying a compressive force to the elongated curved arm to move the pair of spoons inwardly to reduce the distance between the spoons;

positioning the speculum proximate the patient's eye; and releasing the compressive force on the elongated curved arm to allow the curvature portion of one of the pair of spoons to engage the patient's upper eyelid and to allow the curvature portion of the other of the pair of spoons to engage with the patient's lower eyelid.

17. The method of claim 16 further comprising the steps of:

providing a scleral depressor;

applying the scleral depressor to the a scleral surface of the patient's eye; and manipulating the patient's eye by applying a compressive force to the scleral surface of the patient's eye.

18. The method of claim 17 wherein the scleral depressor has a tip portion sized to fit between the spoons as the spoons engage the upper and lower eyelids.

\* \* \* \* \*

UNITED STATES PATENT AND TRADEMARK OFFICE
CERTIFICATE OF CORRECTION

PATENT NO.    : 6,440,065 B1
DATED         : August 27, 2002
INVENTOR(S)   : Robert W. Hered, M.D.

It is certified that error appears in the above-identified patent and that said Letters Patent is hereby corrected as shown below:

<u>Column 8,</u>
Line 7, the word "firedly" should read -- fixedly --.

Signed and Sealed this

Fourth Day of March, 2003

JAMES E. ROGAN
*Director of the United States Patent and Trademark Office*